US012721813B2

(12) United States Patent
Takahashi et al.

(10) Patent No.: US 12,721,813 B2
(45) Date of Patent: Sep. 1, 2026

(54) ARALIADIOL DEXTRIN CYCLODEXTRIN POWDERY PREPARATIONS AND METHOD OF MANUFACTURING SAME

(71) Applicant: ICHIMARU PHARCOS CO., LTD., Gifu (JP)

(72) Inventors: Tatsuji Takahashi, Gifu (JP); Hiroyuki Kojima, Gifu (JP); Toshiaki Fujine, Gifu (JP)

(73) Assignee: ICHIMARU PHARCOS CO., LTD., Gifu (JP)

( * ) Notice: Subject to any disclaimer, the term of this patent is extended or adjusted under 35 U.S.C. 154(b) by 466 days.

(21) Appl. No.: 18/551,868

(22) PCT Filed: Mar. 22, 2022

(86) PCT No.: PCT/JP2022/012976
§ 371 (c)(1),
(2) Date: Dec. 6, 2023

(87) PCT Pub. No.: WO2022/202748
PCT Pub. Date: Sep. 29, 2022

(65) Prior Publication Data

US 2024/0189233 A1 Jun. 13, 2024

(30) Foreign Application Priority Data

Mar. 23, 2021 (JP) ................................ 2021-048187

(51) Int. Cl.
*A61K 9/14* (2006.01)
*A61K 31/047* (2006.01)
*C07C 33/048* (2006.01)

(52) U.S. Cl.
CPC ............ *A61K 9/146* (2013.01); *A61K 31/047* (2013.01); *C07C 33/048* (2013.01); *A61K 2236/331* (2013.01)

(58) Field of Classification Search
None
See application file for complete search history.

(56) References Cited

U.S. PATENT DOCUMENTS

2022/0401377 A1* 12/2022 Hara et al. ........... A61K 31/047

FOREIGN PATENT DOCUMENTS

JP 2005-002005 A 1/2005
WO WO 2021/085232 * 5/2021

OTHER PUBLICATIONS

Cheng et al. "Inhibitory Effect of Human Breast Cancer Cell Proliferation via p21-Mediated G1 Cell Cycle Arrest by Araliadiol Isolated from *Aralia cordata* Thunb.", Planta Med., 2011, 77, pp. 164-168. (Year: 2011).*
Mightysil rp 18 gp, pubCompare, accessed on Mar. 4, 2026 at www.pubcompare.ai/product/DyriCZIBPBHhf-iFSD21/. (Year: 2026).*
International Search Report in PCT/JP2022/012976, mailed May 10, 2022, 4pp.
Sahab Uddin et al., "Nootropic and Anti-Alzheimer's Actions of Medicinal Plants: Molecular Insight into Therapeutic Potential to Alleviate Alzheimer's Neuropathology", Molecular Neurobiology, Nov. 9, 2018, pp. 4925-4944, vol. 56, No. 7, Springer, 1pp.
Written Opinion in PCT/JP2022/012976, mailed May 10, 2022, 11pp.

* cited by examiner

*Primary Examiner* — James H Alstrum-Acevedo
(74) *Attorney, Agent, or Firm* — HAUPTMAN HAM, LLP

(57) ABSTRACT

To provide a stabilized preparation for using Araliadiol as a medicine or a functional food, and a method for manufacturing the same. A powdery preparation that contains Araliadiol, dextrin and cyclodextrin. Preferably, the powdery preparation further contains a macromolecular polysaccharide.

17 Claims, 2 Drawing Sheets

ARALIADIOL DEXTRIN CYCLODEXTRIN POWDERY PREPARATIONS AND METHOD OF MANUFACTURING SAME

RELATED APPLICATIONS

The present application is a National Phase of International Application No. PCT/JP2022/012976 filed Mar. 22, 2022, which claims priority to Japanese Application No. 2021-048187, filed Mar. 23, 2021.

TECHNICAL FIELD

The present invention relates to a stabilized powdery preparation containing araliadiol and a method for production thereof, and the like.

BACKGROUND ART

Gotu kola (*Centella asiatica*; also known as Tsubokusa) is an herb native to India, Indonesia, China, and Southeast Asia, and is used in Ayurveda, a traditional Indian medicine. It is known to have a wide range of effects, including antipyretic, analgesic, anti-inflammatory, and cognitive function improvement. For example, it has been reported that when Gotu kola extract was administered to rats, oxidative stress was reduced and cognitive function was improved, and it is expected to be a therapeutic agent for Alzheimer's disease (see, for example, Non-Patent Literature 1).

By the way, in order to develop such active ingredients as pharmaceuticals and functional foods, it is desirable to be able to stably store them at room temperature for a certain period of time or longer. For example, in order to stabilize vitamins and coenzyme Q10 in pharmaceuticals and foods, a technology has been reported to encapsulate them in cyclodextrins to make a powder composition (see, for example, Patent Literature 1).

CITATION LIST

Non-Patent Literature

[Non-Patent Literature 1] Md Sahab Uddin et al., Nootropic and Anti-Alzheimer's Actions of Medicinal Plants: Molecular Insight into Therapeutic Potential to Alleviate Alzheimer's Neuropathology. Mol Neurobiol. 2019 July; 56 (7): 4925-4944.

Patent Literature

[Patent Literature 1] JP Patent Publication No. 2005-2005

SUMMARY OF INVENTION

Technical Problem

The inventors found that araliadiol, a single compound purified by HPLC from an ethanol extract of Gotu kola, is the main active ingredient for the prevention and/or treatment of neurodegenerative diseases and have already filed an international application (PCT/JP2020/039361). However, the storage stability of preparations containing araliadiol is not yet known.

The problem to be solved by the present invention is to provide a stabilized preparation of araliadiol for use as a medicine, functional food, etc., and a manufacturing method thereof, and the like.

Solution to Problem

In order to solve the above problem, the inventors have studied diligently and found that the above problem can be solved by mixing araliadiol with a specific excipient to make a powdery preparation. In other words, the present invention includes the following embodiments.

[1] A powdery preparation comprising araliadiol, dextrin and cyclodextrin.

[2] The powdery preparation according to [1], further comprising a macromolecular polysaccharide.

[3] The powdery preparation according to [1] or [2], wherein the cyclodextrin is comprised 20% by mass or more of the total amount of the powdery preparation.

[4] The powdery preparation of any one of [1] to [3], wherein the cyclodextrin comprises γ-cyclodextrin.

[5] The powdery preparation of any one of [2] to [4], wherein the macromolecular polysaccharide is gum arabic or gum ghatti.

[6] The powdery preparation according to any one of [1] to [5] for stabilizing araliadiol as an active ingredient.

[7] A process for producing araliadiol, comprising the steps of: extracting a Gotu kola plant body with a mixture of organic solvent and water, passing the extract obtained in the extraction step through a column packed with a hydrophobic synthetic adsorbent to adsorb araliadiol on the hydrophobic synthetic adsorbent, and eluting components adsorbed on the hydrophobic synthetic adsorbent with a mixture of organic solvent and water.

[8] A process for producing a powdery preparation, comprising the steps of: mixing araliadiol, dextrin, and cyclodextrin to obtain a mixed solution; homogenizing the mixed solution to prepare an emulsified solution, and drying the emulsified solution.

[9] The process for producing the powdery preparation according to [8], wherein the cyclodextrin comprises γ-cyclodextrin.

EFFECTS OF THE INVENTION

According to the present invention, it is possible to provide stabilized preparations of araliadiol for use as pharmaceuticals and functional foods, as well as a manufacturing method for such preparations.

DESCRIPTION OF EMBODIMENTS

Figure 1:
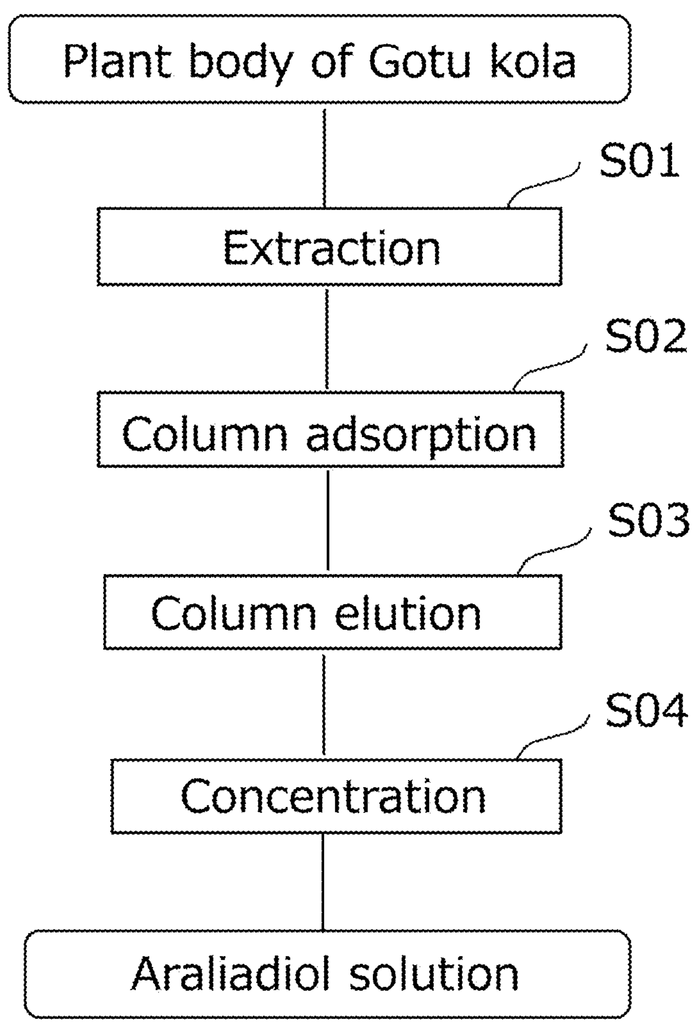
FIG. 1 is a flow diagram showing the steps in the production of araliadiol in one embodiment.

The present invention relates to powdery preparations containing at least araliadiol, dextrin, and cyclodextrin, and preferably also macromolecular polysaccharides. The following is a description of each ingredient in a typical embodiment of the powdery preparation.

Araliadiol

The preparation of the present embodiment contains, as an active ingredient, araliadiol (CAS No. 1354638-93-9) represented by the following formula (1):

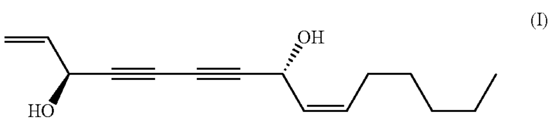 [SMILES: C=C[C@H](O)C#CC#C[C@H](O)/C=C\CCCCC]

The compound represented by the above formula (I) contains chiral carbon atoms at positions 3 and 8, and the double bonds between the carbon atoms at positions 9 and have a cis (Z) stereo configuration. Therefore, the active ingredient may be an optical, racemic and/or geometric isomer with respect to these positions. Naturally occurring araliadiol has also been isolated from ethanol extracts of Udo (*Aralia cordata*) leaves and has been reported to have growth inhibitory activity on human breast cancer cells (Cheng W L et al. (2011) Planta Med; 77: 164-16 8). Araliadiol can be produced from medicinal plants such as Gotu kola and Udo by organic solvent extraction and purification by column chromatography.

The active ingredient may be in the form of a salt or derivative, and when the hydroxy group of the compound represented by formula (I) is moderately acidic, the salts include, for example, metal salts such as aluminum, alkali metal salts such as lithium, sodium or potassium, alkaline earth metal salts such as calcium or magnesium, and ammonium or substituted ammonium salts, such as lower alkyl amines such as triethylamine, hydroxyalkylamines such as 2-hydroxyethylamine, bis-(2-hydroxyethyl)-amine or tri-(2-hydroxyethyl)-amine, salts with cycloalkylamines such as bicyclohexylamine, or procaine, dibenzylpiperidine, N-benzyl-β-phenethylamine, dehydroabietylamine, N, N'-bisdehydroabietylamine, glucamine, N-methylglucamine, or salts with pyridine-type bases such as pyridine, collidine, quinine or quinoline. The hydroxy group of the compound represented by formula (I) may also be acylated, alkylated, phosphorylated or boronated derivatives. As used herein, therefore, the term "araliadiol" includes compounds represented by the above formula (I), isomers thereof or derivatives thereof, or salts thereof.

The amount of araliadiol in the preparation of this embodiment is not particularly limited, as long as it contains an effective amount of araliadiol to produce the desired effect (e.g., the effect of preventing or treating a disease or condition that presents a disturbance in brain function), for example, when the entire preparation is 100 mass percent, The lower limit of araliadiol content is preferably 1 ppm (0.0001% by mass) or more, more preferably 10 ppm (0.001% by mass) or more, and even more preferably 100 ppm (0.01% by mass) or more.

The upper limit of araliadiol content is preferably 50% by mass or less, more preferably 40% by mass, and even more preferably 30% by mass or less.

(Dextrin)

Dextrin is a partially hydrolyzed form of starch. Depending on the degree of partial hydrolysis of starch, there are various types of dextrins with different molecular weights. The DE (Dextrose Equivalent) value is generally used as an indicator to understand the degree of partial hydrolysis of starch (i.e., the molecular weight distribution of dextrins). A high DE value means that the starch is hydrolyzed to a smaller average molecular weight and has characteristics similar to glucose, while a low DE value means that the degree of degradation is low and similar to starch. DE values range from 0 to 100. In this document, "DE" is a value obtained by the Wilstetter-Schudel method and calculated from the formula [(mass of directly reduced sugar (indicated as glucose))/(mass of solid content)]×100.

In this embodiment, dextrins with a DE of 20 or less are preferably used among dextrins. The use of dextrins with a DE of 20 or less contributes to improved dispersibility and stability when made into a powdery preparation. Dextrins used in the present invention are more preferably dextrins with a DE of 5 or less. Dextrins of DE 5 or less used in the present invention are commercially available, and commercially available dextrins include, for example, corn-derived dextrins of DE 4 (Pinedex #100: manufactured by Matsutani Chemical Industry Co., Ltd.) and Sandec #30 (DE 2-5: manufactured by Sanwa Starch Industry Co.

The content of dextrin is not particularly limited, but when the total mass of the preparation of this embodiment is 100% by mass, The lower limit of the dextrin content is preferably 10% by mass or more, more preferably 15% by mass, even more preferably 20% by mass, The upper limit of the dextrin content is preferably 50% by mass or less, more preferably 45% by mass and even more preferably 40% by mass or less.

(Cyclodextrin)

Cyclodextrins are a type of cyclic oligosaccharide with a ring structure formed by several molecules of D-glucose joined by α(1→4) glucoside bonds. These cyclodextrins are not particularly limited and include, for example, α-cyclodextrin (αCD, six-membered sugar ring molecules), β-cyclodextrin (βCD, seven-membered sugar ring molecules), γ-cyclodextrin (γCD, eight-membered sugar ring molecules) and others.), etc., of which γCD is particularly preferred. This is because it can contain araliadiol in higher concentrations and also enable a highly stable powdery preparation to be obtained. In addition, only one of these may be contained, or two or more may be used in combination.

In addition, cyclodextrins with branched side chains such as glucose and maltose (hereinafter simply referred to as "branched cyclodextrins") as the above cyclodextrins and cyclodextrins with substituents such as methyl, hydroxypropyl and acetyl groups (hereinafter simply referred to as "cyclodextrin derivatives") may be used. This is because the inclusion of these substances will result in a powdery preparation that is water-soluble. Cyclodextrin alone may be used, or a mixture with cyclodextrin derivatives may be used, but cyclodextrin alone is preferred.

The cyclodextrin in this embodiment of the powdery preparation acts as an excipient as well as a stabilizer of the active ingredient. As used herein, an excipient is an additive to improve handling, molding, and convenient administration. Although not bound by any particular theory, it is believed that cyclodextrin acts as a stabilizer by encapsulating the active ingredient, araliadiol, thereby deterring oxidation by heat or light from the outside world or making it less susceptible to coexisting substances.

From the viewpoint of improving the storage stability of araliadiol, the content of cyclodextrin in the powdery preparation of this embodiment is 20% by mass or more, more preferably 30% by mass or more and still more preferably 40% by mass or more. The upper limit of cyclodextrin content is preferably 80% by mass or less, 70% by mass or less is more preferable, and 60% by mass or less is even more preferable. If the cyclodextrin content is too high, it is difficult to obtain a powdery preparation with excellent flowability.

(Macromolecular Polysaccharides)

Macromolecular polysaccharides can be widely selected from natural and synthetic macromolecular polysaccharides, such as guar gum, locust bean gum, Tara gum, tamarind gum, glucomannan, xanthan gum, soy fiber, corn fiber, okara fiber, gum arabic, gum ghatti, pectin, gellan gum, pullulan, cardran, agar, sodium alginate, cellulose, and carboxymethylcellulose. One or more of these can be selected for use. In particular, in this embodiment, it is more preferred to use one or more of gum arabic, gum ghatti, carrageenan, guar gum, tamarind gum, Tara gum, glucomannan, xanthan gum, locust bean gum, and corn fiber.

Gum arabic as one embodiment is a gum-like secretion obtained from the stem and branches of *Acacia senegal* Willdenow or other allied plants (Leguminosae). Gum arabic consists of sugars such as galactose, arabinose, rhamnose, glucuronic acid and 4-O-methylglucuronic acid, and about 2% protein, including amino acids such as hydroxyproline, proline and serine. Gum arabic is commercially available and commercially available products include, for example, gum arabic HP powder (manufactured by DSP Gokyo Food & Chemical Co.

Another embodiment of gum ghatti is an amorphous, translucent secretion obtained from a ghatti tree (*Anogeissus latifolia*) of the family Sicunciaceae, found in the dry deciduous forest zone of India. It is a water-soluble gum containing about 3% protein in an acidic complex polysaccharide composed of l-arabinose, d-galactose, d-glucuronic acid, and other sugars. Gum ghatti is commercially available, and commercially available products include, for example, GATICOL SS (manufactured by SAN-EI YAKUHIN BOEKI CO., LTD.

The content of macromolecular polysaccharides is not particularly limited, but when the total mass of the preparation of this embodiment is 100% by mass, The lower limit of the content of macromolecular polysaccharides is preferably 5% by mass or more, more preferably 6% by mass, more preferably 7% by mass and even more preferably 8% by mass, The upper limit of the content of macromolecular polysaccharides is preferably 20% by mass or less, more preferably 15% by mass, even more preferably 12% by mass or less.

(Other Additives)

Araliadiol, the active ingredient in this embodiment, is oil-soluble and difficult to add to food and beverages as it is due to its poor dispersibility in water, so a solution of araliadiol dissolved in a water-miscible organic solvent can be mixed with other additives such as oils and surfactants to form an emulsion, which is then dried into a powdery preparation.

(1) Fats and Oils

Fats and oils include, avocado oil, amani-oil, almond oil, wikyo oil, egoma oil, olive oil, orange oil, orange raffer oil, cocoa oil, chamomile oil, carrot oil, cucumber oil, kyunin oil, kukui-nut oil, walnut oil, wheat germ oil, sesame oil, rice oil, rice bran oil, sasanqua oil, safflower oil, salad oil, shea oil, soybean oil, tea oil, evening primrose oil, camellia oil, corn oil, rapeseed oil, persic oil, safflower oil, castor oil, sunflower oil, grape seed oil, hazelnut oil, macadamia nut oil, cottonseed oil, meadowfoam oil, peanut oil, rose hip oil, turtle oil, mink oil, egg yolk oil, cocoa fat, palm oil, palm kernel oil, mokuro, coconut oil, fish oil, whale oil, shark oil, liver oil, beef fat, pork fat, chicken oil, rabbit fat, sheep fat, horse fat, or hydrogenated products of these oils and fats, or derivatives thereof.

(2) Surfactants

Surfactants include, but are not limited to, at least one sucrose fatty acid ester and polyglycerol fatty acid ester. Both of these can act as surfactants and reduce the average particle size of emulsified particles when the emulsion composition is prepared.

The sucrose fatty acid esters used in this embodiment are preferably those with a fatty acid carbon number of 12 or more from the viewpoint of surface activity, and those with a carbon number of 12 to 20 are more preferred. By setting the carbon number to 12 or more, it may be possible to make emulsion particles with a smaller average particle diameter. Sucrose fatty acid esters include sucrose dioleate, sucrose distearate, sucrose dipalmitate, sucrose dimyristate, sucrose dilaurate, sucrose monooleate, sucrose monostearate, sucrose monopalmitate, sucrose monomyristate, sucrose monolaurate, etc. Among these, sucrose monoesters are preferred, especially sucrose monolaurate and sucrose monooleate. In the present invention, these sucrose fatty acid esters can be used alone or in mixture.

Commercial products include, for example, Ryoto Sugar Esters S-070, S-170, S-270, S-370, S-370F, S-570, S-770, S-970, S-1170, S-1170F, S-1570, S-1670, P-070, P-170, P-1570, P-1670, M-1695, O-170, O-1570, DK Ester SS, F160, F140, F110, F90, F70, F50, F-A50, F-20W, F-10, F-A10E, manufactured by Dai-ichi Kogyo Seiyaku Co, Cosmelike B-30, S-10, S-50, S-70, S-110, S-160, S-190, SA-10, SA-50, P-10, P-160, M-160, L-10, L-50, L-160, L-150A, L-160A, R-10, R-20, O-10, O-150, etc. The following are examples of such products.

Polyglycerol fatty acid esters used in this embodiment are esters of polyglycerol with an average degree of polymerization of 2 or more, preferably 6 to 15, more preferably 8 to 10, and fatty acids with carbon numbers from 8 to 18, such as caprylic acid, capric acid, lauric acid, myristic acid, palmitic acid, stearic acid, oleic acid and linoleic acid. Preferred examples of polyglycerol fatty acid esters are hexaglycerol monooleate, hexaglycerol monostearate, hexaglycerol monopalmitate, hexaglycerol monomyristate, hexaglycerol monolaurate, decaglycerin monooleate, decaglycerin monostearate, decaglycerin monopalmitate, decaglycerin monomyristate, decaglycerin monolaurate, etc.

Among these, decaglycerin monooleate (HLB=12), decaglycerin monostearate (HLB=12), decaglycerin monopalmitate (HLB=13), decaglycerin monomyristate (HLB=14), and decaglycerin monolaurate (HLB=16), etc. are more preferred. These polyglycerol fatty acid esters can be used alone or in mixtures.

Commercial products include, for example, NIKKOL DGMS, NIKKOL DGMO-CV, NIKKOL DGMO-90V, NIKKOL Decaglyn PR-20, manufactured by Nikko Chemicals Co, Ryoto Polyglyester L-7D, L-10D, M-10D, manufactured by Mitsubishi Chemical Foods, Inc., Sunsoft Q-17UL, Sunsoft Q-14S, and Sunsoft A-141C made by Taiyo Kagaku Co, and Poem DO-100, Poem J-0021, etc. manufactured by Riken Vitamin Co., Ltd.

(Powdery Preparations and their Uses)

The "powdery preparation" of the present invention and this embodiment include not only powders, but also, for example, tablets, granules, and dispersions prepared by forming the powder.

Compositions, etc., containing the powdery preparation of this embodiment (including the powdery preparation, capsules containing the powdery preparation, etc.) contain at least three ingredients (araliadiol, dextrin and cyclodextrin) that are effective in demonstrating the desired effects of araliadiol (such as improvement of cognitive function) and have storage stability. In certain embodiments, for example, this powdery preparation contains:

(a) 0.0001 to 50% by mass of araliadiol;
(b) 5 to 50% by mass of dextrin;
(c) 10 to 80% by mass of cyclodextrin; and
(d) optionally, up to 50% by mass of other additives.

In order to achieve the desired effect, a composition or the like containing the powder preparation of this embodiment (including the powdery preparation) may be administered to a human, for example, at a dose of 1 to 10 mg/day of araliadiol. The method of administration may be, for example, oral, topical (including ophthalmic, vaginal, intrarectal, intranasal, and transdermal), or parenteral administration. Parenteral administration includes intravenous injection or infusion, subcutaneous, intraperitoneal or intramuscular injection, pulmonary administration by inhalation or aspiration, intrathecal administration, intracerebroventricular administration, etc.

The powdery preparation containing araliadiol of this embodiment and the composition containing the powdery preparation are useful, for example, for the prevention or treatment of diseases or conditions presenting disorders of brain function. Such diseases or conditions presenting brain dysfunction include, for example, dementia (e.g., senile dementia, Alzheimer's disease, cerebrovascular dementia, post-traumatic dementia, dementia caused by brain tumors, dementia caused by chronic subdural hematoma, dementia caused by normal pressure brain edema, post-meningitis dementia, and Parkinsonian dementia, etc.), non-dementia cognitive impairment (e.g., mild cognitive impairment (MCI)), and memory or learning impairment (e.g., memory and learning impairment associated with brain development disorders).

When the composition containing the powdery preparation of this embodiment is used as a food or beverage, for example, food with the concept of prevention, improvement, or enhancement of cognitive function decline and labeled to that effect as necessary, food with a functional claim, food for specified health uses, food for the sick, and supplements are included. When using the powdery preparation of this embodiment to manufacture a dietary supplement, the powdery preparation can be tablet-formed as it is, but additives normally used in preparations, such as starch, lactose, white sugar, mannitol, carboxymethylcellulose, cornstarch, inorganic salts, etc., can be added as necessary.

On the other hand, if the composition containing the powdery preparation of this embodiment were to be used as a pharmaceutical product (including quasi-drugs and the like), it would contain a therapeutically effective amount of araliadiol and would be administered by any of the dosage forms permitted for drugs that provide similar utility. The therapeutically effective dose will be set according to a number of factors, including the severity of the disease to be treated, the age and relative health of the subject, the route and form of administration, the indication for which administration is directed, and the preference and experience of the physician involved. A person skilled in the art of treating such diseases will be able to determine the therapeutically effective amount of araliadiol for a given disease without more experimentation than necessary and relying on personal knowledge and the disclosure of this application.

(Process for Producing Araliadiol and Powdery Preparations Containing Araliadiol)

Other aspects of the invention provide a process for producing araliadiol. FIG. 1 shows a flow diagram of the production of araliadiol. The process comprises an extraction step (S01) in which the Gotu kola plant body is extracted with a mixture of organic solvents and/or water, and a column adsorption step (S02) in which the resulting extract is passed through a column packed with a hydrophobic synthetic adsorbent to adsorb araliadiol to it, a column elution step (S03) in which the component adsorbed on the hydrophobic synthetic adsorbent is eluted with a mixture of organic solvent and water to obtain an eluted fraction containing araliadiol, and the concentration step (S04) to concentrate the extracted solution.

The Gotu kola plant used in the extraction step (S01) is extracted from the flower, flower ear, fruit, stem, leaf, petiole, branch, branch leaf, rhizome, root, seed, or whole plant of Gotu kola, or other species of the same genus may be used. The extracting method is water or organic solvent (ethanol solution, etc.) or a mixture thereof. For example, 30-90% ethanol solution, preferably 50% ethanol solution, is used as the extracting solvent. In this embodiment, it is preferable to use an ethanol extract of the whole Gotu kola plant.

The adsorbent used in the column adsorption step (S02) is not limited to any hydrophobic synthetic adsorbent that can adsorb highly hydrophobic araliadiol, but an aromatic synthetic adsorbent is preferred. A hydrophobic synthetic adsorbent is a hydrophobic adsorbent composed of a cross-linked polymer with a porous structure, which adsorbs various organic substances in solution through physical interaction between the pores and the adsorbed substances. The type of hydrophobic synthetic adsorbent is not limited to the extent that the purpose of the invention can be achieved, and may be selected as appropriate. However, it is preferable to use an aromatic synthetic adsorbent because it improves the removal efficiency of impurities. "Aromatic synthetic adsorbent" means that the cross-linked polymer that constitutes the synthetic adsorbent has an aromatic ring group such as a benzene ring. An example of an aromatic synthetic adsorbent is a porous material made of styrene-divinylbenzene copolymer. Aromatic synthetic adsorbents include DIAION HP20, DIAION HP21, SEPABEADS SP825, SEPABEADS SP850, SEPABEADS SP700, SEPABEADS SP270 (These are trade names of Mitsubishi Chemical Corporation), Amberlite XAD4, Amberlite XAD16HP, Amberlite XAD1180, Amberlite XAD2000 (These are trade names of Rohm and Haas Co., Ltd.), etc. can be exemplified.

Figure 2:
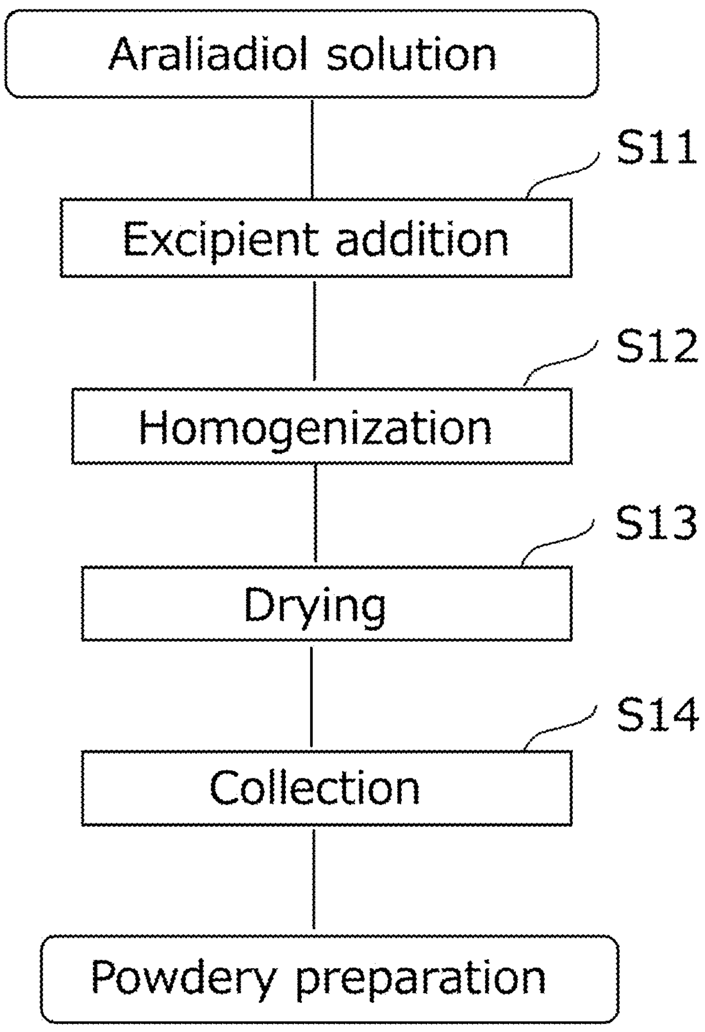
FIG. 2 is a flow diagram of the process for producing a powdery preparation containing araliadiol.

A further aspect of the invention is a process for producing a powdery preparation containing araliadiol, dextrin and cyclodextrin. FIG. 2 shows a flow diagram of the steps involved in producing a powdery preparation by the process. The process comprises an excipient addition step (S11) in which dextrin, cyclodextrin and the like are added to an araliadiol solution to obtain a mixed solution, a homogenization step (S12) in which the mixed solution obtained at S11 is homogenized to prepare an emulsified solution, a drying step (S13) in which the emulsified solution obtained at S12 is dried, and a collection step (S14) for collecting the powdery preparation after drying.

The excipient addition step (S11) can be achieved by mixing the oil phase, in which araliadiol is added and dissolved, with the aqueous phase, in which excipients such as dextrins and cyclodextrins are dissolved.

In the homogenization step (S12), the above mixture is homogenized to prepare an emulsion. The emulsification method is not restricted, and various emulsifiers conventionally used in food and beverages, such as the macromolecular polysaccharides and surfactants mentioned above, are added and emulsified using a homo-mixer, colloid mill, rotating disc homogenizer, high-pressure homogenizer, etc. to obtain an emulsion with excellent stability.

The emulsion thus obtained is then subjected to drying in a drying step (S13). The drying methods applicable to this production process may be any of the methods normally used for this application, such as spray drying, freeze drying, vacuum drying, shelf drying, belt drying and drum drying. Of these, spray drying and freeze drying are preferred from the viewpoint of powder handling.

The invention will now be described in more detail with examples, but the invention is not restricted in any way by these examples. In the following examples, the unit "%" of the numerical values indicating the added amount of various components means "% by mass".

EXAMPLES

[Example 1] Preparation of Gotu Kola Extract

To 6 g of dried and crushed Gotu kola leaves, stems, or whole plants, 75 mL of 30-90% ethanol was added, respectively, and extraction was performed for 7 days at room temperature with occasional stirring. The resulting extracts were filtered and used as test samples. The analysis of araliadiol in these test samples was performed under the following conditions.

Column: Mightysil RP-18 GP 250-4.6 (5 μm)
Eluent: $CH_3CN$: 0.1% phosphoric acid=52:48
Flow rate: 1.0 mL/min
Analysis temperature: 40° C.
Detection: UV 210 nm The content of araliadiol in Gotu kola extracts varied depending on the region and part of Gotu kola, but the 50% ethanol extract had the highest recovery. Other components such as phenylpropanoids, flavonoids, and triterpenoids are also extracted simultaneously in the 50% ethanol extract of Gotu kola. Under the HPLC analysis conditions described above, araliadiol was found to elute at a retention time of approximately 24 minutes. In the following experiments, the purification stage of Gotu kola extract and samples stored under various conditions were analyzed by HPLC under the same conditions as above, and the concentration of araliadiol in the samples was determined by comparing the peak area of the standard product.

[Example 2] Purification of Gotu Kola Extract (Preparation of Araliadiol Concentrate)

To 100 g of the whole Gotu kola plant, 1500 g of 50% ethanol was added, extracted at room temperature for 7 days, and filtered to obtain the extract. The extract was applied to a column packed with about 500 mL of aromatic synthetic adsorbent (e.g., DIAION HP20), and after elution of the other components with about 1500 mL of 50% by volume ethanol, araliadiol was eluted with 55% by volume ethanol. The fraction containing araliadiol was concentrated to obtain 100 mL of the concentrated solution. This concentrated solution contained approximately 750 μg/mL of araliadiol. The concentrated solution was evaporated to dryness with ethanol and water in a 50° C. water bath and dissolved again in ethanol, and the peak of araliadiol was measured by HPLC, resulting in a concentration of 296.2 μg/mL of araliadiol.

[Test Example 1] Determination of Storage Stability of Gotu Kola Extract

The Gotu kola extract obtained in Example 1 was further concentrated and dried, and the powder was sealed in a heat-sealed Lamizip package and stored. After one month and three months of storage at −20° C. and 40° C., respectively, the sample (the hermetically sealed powder) was dissolved in ethanol and analyzed by HPLC under the same conditions as in Example 1. Table 1 below shows the amount of araliadiol remaining in the samples after one month and three months of storage, where the amount of araliadiol in the sample immediately after the start of storage (day 0) was set at 100. In Table 1, "−20° C." indicates the group in which the sample was stored at −20° C., and "40° C." indicates the group in which the sample was stored at 40° C.

TABLE 1

| Storage period | Storage at −20° C. | Storage at 40° C. |
|---|---|---|
| 0 day | 100 | 100 |
| 1 month | 97.9 | 91.5 |
| 3 months | 97.0 | 79.3 |

As shown in Table 1, the amount of araliadiol in the sample after 3 months of storage at 40° C. from the start of storage was found to have decreased to 79.3. It is believed that the decomposition of araliadiol is accelerated at a higher storage temperature.

[Test Example 2] Accelerated Degradation Test of Araliadiol Concentrate Part 1

An accelerated degradation test at 40° C. was conducted using the following compositions (Powder 1 and Powder 2). The results of this test are shown in Table 2 below.

Powder 1: Powder 1 is a mixture of 0.1% by mass of the araliadiol concentrate obtained in Example 2 and 99.9% by mass of highly branched-chain dextrin (product name: Cluster Dextrin, manufactured by NIHON SHOKUHIN KAKO CO., LTD.

Powder 2: Powder 2 is a mixture of 0.1% by mass of araliadiol concentrate obtained in Example 2 and 99.9% by mass of starch degradation product (Pinedex #100 (DE 3.8), Matsutani Chemical Industry Co., Ltd.)

In Table 2, the amount of araliadiol in the sample immediately after the start of storage (day 0) was set to 100.

TABLE 2

| | Acceleration test (40° C.) | |
|---|---|---|
| | Powder 1 | Powder 2 |
| Day 0 | 100.0 | 100.0 |
| 1 month | 17.2 | 19.3 |

The results shown in Table 2 (values of 17.2 and 19.3 for the first month of storage) indicate that the addition of common excipients from conventional technology, such as highly branched cyclic dextrin and starch degradation products, alone could not solve the problem of improving the storage stability of araliadiol.

[Test Example 3] Accelerated Degradation Test of Araliadiol Purified Products, Part 2

The results of an accelerated degradation test at 60° C. using the following compositions (Composition 1, Composition 2, and Composition 3) are shown in Table 3 below. In Table 3, the amount of araliadiol in the samples immediately after the start of storage (0 day) was set as 100 (100%).

Composition 1: A mixture of araliadiol concentrate obtained in Example 2 (0.1% by mass) and Dixie Pearl SD-20 (99.9% by mass). This Dixie Pearl SD-20 (ENSUIKO Sugar Refining Co., Ltd.) is a product containing cyclodextrin and dextrin.

Composition 2: A mixture of araliadiol concentrate obtained in Example 2 (0.1% by mass) and cyclodextrin-β (99.9% by mass). The product name of cyclodextrin-β is "CELDEX B-100" (NIHON SHOKUHIN KAKO CO., LTD.).

Composition 3: A mixture of the araliadiol concentrate obtained in Example 2 (0.1% by mass) and olive oil (99.9% by mass). The olive oil is olive oil manufactured by KANTO CHEMICAL CO., INC.

The accelerated degradation test at 60° C. is based on the Arrhenius formula and assumes the following (Shigeyuki Sakaue and Akito Kawase: Storage Stability Testing of Pharmaceuticals, SCAS NEWS, 2000-1, p. 7-11).

14 days from the start of storage: In the accelerated degradation test at 40° C., it is assumed to be 2 years from the start of storage.

TABLE 3

| Accelerated test (60° C.) | | | |
|---|---|---|---|
| | Composition 1 | Composition 2 | Composition 3 |
| Day 0 | 100 | 100 | 100 |
| Day 14 | 90.2 | 79.5 | 47.8 |

As shown in Table 3, when a mixture of cyclodextrin and dextrin was used as an excipient, 90% or more (at 40° C., 90% or more at 2 years of storage) of araliadiol remained in the group with 14 days of storage, compared to the group with 0 days.

[Example 3] Production of Preparation 1

A powdery preparation was produced using the araliadiol concentrate obtained in Example 2 and various excipients. First, each of the aqueous components consisting of polyglycerol fatty acid esters, sucrose fatty acid esters, cyclodextrins, gum arabic, and dextrins in predetermined amounts shown in Table 4 were mixed and dissolved in purified water heated to 85° C. Next, the oil components of araliadiol concentrate, rice oil, and tocopherol in the predetermined amounts shown in Table 4 were mixed and dissolved in heated water at 50° C. The aqueous and oily component mixtures thus prepared were mixed, made up to about 100 mL with water, and then homogenized using a precision emulsification-dispersion machine, CLEAMIX (M Technique Co., Ltd.) The supernatant obtained by centrifugation at 13,000 rpm for 5 min was concentrated until water was removed, and lyophilized using a lyophilizer (FDU-2100, Tokyo Rika Kikai Co. Ltd. The following day, the obtained lyophilized material was ground using a lab milling machine, placed in Lamizip, and stored under the specified conditions.

TABLE 4

| Preparation 1 | |
|---|---|
| Ingredient Name | Composition (%) |
| Araliadiol concentrate (Example 2) | 0.1 |
| Rice oil | 10 |
| Polyglycerol fatty acid ester | 2.5 |
| Sucrose fatty acid esters | 7.5 |
| Cyclodextrin (γ) | 42.9 |
| Gum Arabic | 9 |
| Dextrin | 27 |
| Tocopherol | 1 |
| Total | 100 |

[Example 4] Production of Preparation 2

Preparation 2 with the composition shown in Table 5 below was prepared in the same manner as in Example 3, except that gum ghatti was used instead of gum arabic.

TABLE 5

| Preparation 2 | |
|---|---|
| Ingredient Name | Composition (%) |
| Araliadiol concentrate (Example 2) | 0.1 |
| Rice oil | 10 |
| Polyglycerol fatty acid ester | 2.5 |
| Sucrose fatty acid esters | 7.5 |
| Cyclodextrin (γ) | 42.9 |
| Gum ghatti | 9 |
| Dextrin | 27 |
| Tocopherol | 1 |
| Total | 100 |

[Example 5] Production of Preparation 3

Preparation 3 was produced in the same manner as in Example 3, with the composition shown in Table 6 below.

TABLE 6

| Preparation 3 | |
|---|---|
| Ingredient Name | Composition |
| Araliadiol concentrate (Example 2) | 0.1 |
| Cyclodextrin (γ) | 55 |
| Gum Arabic | 9.9 |
| Dextrin | 35 |
| Total | 100 |

The product names and manufacturers of the various excipient ingredients used in Examples 3-5 are listed in Table 7 below.

TABLE 7

| Ingredient Name | Product Name | Manufacturer |
|---|---|---|
| Rice oil | Rice Salad Oil (Business use) | Sanwa Yushi Co., Ltd. |
| Polyglycerol fatty acid ester | Ryoto Polygly Ester L-7D | Mitsubishi-Chemical Foods Corporation |
| Sucrose fatty acid esters | DK ester F-10 | DKS Co. Ltd. |
| Cyclodextrin (γ) | CAVAMAX W8 FOOD | CycloChem Co., Ltd. |
| Gum Arabic | Gum Arabic HP powder | DSP Gokyo Food & Chemical Co., Ltd. |
| Gum ghatti | Ghatticor SS | SAN-EI YAKUHIN BOEKI CO., LTD. |
| Dextrin | Pinedex #1 | Matsutani Chemical Industry Co., Ltd. |
| Tocopherol | E-MIX A40 | Mitsubishi-Chemical Foods Corporation |

Test Example 4

Table 8 below shows the results of accelerated degradation tests conducted in the same manner as in Test Example 3 using preparations 1 to 3 produced in Examples 3 to 5.

The accelerated degradation test at 60° C. was based on the Arrhenius formula (Shigeyuki Sakaue and Akito Kawase: Storage Stability Tests of Pharmaceutical Products, SCAS NEWS 2000-1 p. 7-11), assuming the followings. The storage start date was set to 0 day (marked as 0 day in Table 8).

- 7 days from the start of storage: In the accelerated degradation test at 40° C., it is assumed to be 1 year from the start of storage. In Table 8, it is marked as 7 days.
- 14 days from the start of storage: In the accelerated degradation test at 40° C., it is assumed to be 2 years from the start of storage. In Table 8, it is marked as 14 days.

In Table 8, the amount of araliadiol in the sample immediately after the start of storage (day 0) was set to 100. In Table 8, the group with Preparation 1 as the sample is referred to as "Preparation 1," the group with Preparation 2 as the sample is referred to as "Preparation 2," and the group with Preparation 3 as the sample is referred to as "Preparation 3."

TABLE 8

| | Accelerated test (60° C.) | | |
|---|---|---|---|
| | Preparation 1 | Preparation 2 | Preparation 3 |
| Day 0 | 100 | 100 | 100 |
| Day 7 | 100 | 100 | 99 |
| Day 14 | 100 | 93.7 | 92.3 |

The results shown in Table 8 indicate that the residual amount of araliadiol in both groups was 90% or more at 14 days, compared to 0 days.

The above description of the embodiment of the invention (including examples) has been given with reference to the drawings. The specific configuration of the invention is not limited to this, and design changes, etc., are included in the invention to the extent that they do not depart from the gist of the invention.

Since the powdery preparation of the present invention has stabilized araliadiol (e.g., it is presumed to be stable even after being stored at room temperature for a period of one year or longer), it may be used, for example, as a pharmaceutical or functional food containing said powdery preparation.

The invention claimed is:

1. A powdery preparation comprising araliadiol, dextrin and cyclodextrin.

2. The powdery preparation according to claim 1, further comprising a macromolecular polysaccharide.

3. The powdery preparation of claim 2, wherein the macromolecular polysaccharide is gum arabic or gum ghatti.

4. The powdery preparation according to claim 3, for stabilizing araliadiol as an active ingredient.

5. The powdery preparation according to claim 2, wherein the cyclodextrin is comprised 20% by mass or more of the total amount of the powdery preparation.

6. The powdery preparation of claim 2, wherein the cyclodextrin comprises γ-cyclodextrin.

7. The powdery preparation according to claim 2, for stabilizing araliadiol as an active ingredient.

8. The powdery preparation according to claim 1, wherein the cyclodextrin is comprised 20% by mass or more of the total amount of the powdery preparation.

9. The powdery preparation of claim 8, wherein the cyclodextrin comprises γ-cyclodextrin.

10. The powdery preparation of claim 8, wherein the macromolecular polysaccharide is gum arabic or gum ghatti.

11. The powdery preparation according to claim 8, for stabilizing araliadiol as an active ingredient.

12. The powdery preparation of claim 1, wherein the cyclodextrin comprises γ-cyclodextrin.

13. The powdery preparation of claim 12, wherein the macromolecular polysaccharide is gum arabic or gum ghatti.

14. The powdery preparation according to claim 12, for stabilizing araliadiol as an active ingredient.

15. The powdery preparation according to claim 1, for stabilizing araliadiol as an active ingredient.

16. A process for producing a powdery preparation, comprising the steps of:

mixing araliadiol, dextrin, and cyclodextrin to obtain a mixed solution, homogenizing the mixed solution to prepare an emulsified solution; and drying the emulsified solution.

17. The process for producing the powdery preparation according to claim 16, wherein the cyclodextrin comprises γ-cyclodextrin.

* * * * *